(12) United States Patent
Bruchert et al.

(10) Patent No.: US 6,830,610 B1
(45) Date of Patent: Dec. 14, 2004

(54) METHOD FOR INCREASING THE TENSILE, BREAKING AND FLEXURAL STRENGTH OF COLORED LEADS AND COLORED PENCILS CONTAINING THE SAME

(75) Inventors: Werner Bruchert, Oberasbach (DE); Christian Sprogar, Bubenreuth (DE); Willy Weiss, Altdorf (DE)

(73) Assignee: Schwan-Stabilo Cosmetics GmbH & Co. KG, Heroldsberg (DE)

( * ) Notice: Subject to any disclaimer, the term of this patent is extended or adjusted under 35 U.S.C. 154(b) by 0 days.

(21) Appl. No.: 09/936,719

(22) PCT Filed: Mar. 10, 2000

(86) PCT No.: PCT/EP00/02137

§ 371 (c)(1),
(2), (4) Date: Apr. 15, 2003

(87) PCT Pub. No.: WO00/55264

PCT Pub. Date: Sep. 21, 2000

(30) Foreign Application Priority Data

Mar. 16, 1999 (DE) .......................................... 199 11 748

(51) Int. Cl.$^7$ ............................ C09D 13/00; A61K 7/00
(52) U.S. Cl. ..................................... 106/31.11; 424/401
(58) Field of Search ........................ 106/31.11; 424/401

(56) References Cited

U.S. PATENT DOCUMENTS

| | | | | | |
|---|---|---|---|---|---|
| 5,318,622 | A | * | 6/1994 | Kitazawa et al. | 106/31.11 |
| 5,346,540 | A | * | 9/1994 | Schlennert | 106/31.11 |
| 5,399,342 | A | * | 3/1995 | Krzysik | 424/59 |
| 5,451,610 | A | * | 9/1995 | Krzysik | 424/63 |
| 5,460,804 | A | * | 10/1995 | Krzysik | 424/60 |
| 5,512,272 | A | * | 4/1996 | Krzysik | 424/59 |
| 5,595,700 | A | * | 1/1997 | Kitazawa | 264/211 |
| 5,807,562 | A | * | 9/1998 | Ami | 424/401 |
| 6,395,076 | B1 | * | 5/2002 | Hashimoto | 106/31.11 |
| 6,511,533 | B2 | * | 1/2003 | Hashimoto | 106/31.11 |

* cited by examiner

*Primary Examiner*—Mark L. Bell
*Assistant Examiner*—Veronica F. Faison
(74) *Attorney, Agent, or Firm*—Bachman & LaPointe, P.C.

(57) ABSTRACT

A method for increasing the tensile, breaking and flexural strength of coloured leads. The method is characterized in that 1 to 50 percent by weight alkyl and/or hydroxyalkyl cellulose which are soluble in organic solvents and whose alkyl radicals can be straight-chained or branched are added to the lead substance. The invention also relates to coloured pencils containing said coloured leads.

18 Claims, No Drawings

METHOD FOR INCREASING THE TENSILE, BREAKING AND FLEXURAL STRENGTH OF COLORED LEADS AND COLORED PENCILS CONTAINING THE SAME

BACKGROUND OF THE INVENTION

The invention relates to a method of increasing the tensile strength, breaking strength and flexural strength of colored leads and to colored pencils containing such leads.

Colored leads are leads containing pigments, color lakes or dyes, which are used for colored pencils and cosmetics pencils. On the one hand, colored leads should be easy to apply, but must be solid enough to enable processing. Thus, when used in cosmetics pencils, for example, they should be able to be applied gently and softly to delicate areas of skin and readily and intensively impart color upon application. For this reason, they do not generally have a crystalline structure, but exhibit thixotropic behavior and desirably have only a low breaking strength. However, as result of this their tensile strength and flexural strength is also low, which is disadvantageous. During shaping, the proportion of waste is high since the leads readily break when removed from the mold or when subjected to mechanical stress. Particularly in the case of leads which have an unfavorable length to diameter ratio, for example a diameter of from 2 to 6 mm for a length up to 25 to 50 mm, the risk of breakage is high.

The low strength, in particular tensile strength and flexural strength, has proven particularly disadvantageous if thin colored leads having a diameter of less than 6 mm are to be inserted into a rotating pencil where, inserted into a rotary mechanism, they can be rotated out and back, but are not mechanically supported.

In the field of cosmetics pencils, so called "liners"—especially for eyeliner pencils and lipliner pencils, for example—which are supplied inserted into rotary mechanisms, are popular. These liners do not have to be sharpened and the lead, when it is not being used, is protected in the liner sleeve.

Colored leads are usually produced by pouring a homogenized basic mass based on fat/wax mixtures, which, apart from the color-imparting pigments, may comprise further additives, into a mold, or extruding it. For use, the lead is either embedded in wood, poured into preshaped sleeves of wood or plastic or the like, or inserted into a rotary mechanism.

If casting molds are used, considerable forces of adhesion arise in the cooled mold, which, despite the use of release agents, readily leads to tearing of the castings and thus to wastage. Moreover, extensive cleaning operations in the casting plant are required. The insertion of the colored leads into a rotary mechanism and the rotating out of the leads also frequently leads to breakage.

It is therefore an object of the invention to overcome the disadvantages associated hitherto with colored leads and to improve known pencil compositions such that the tensile strength and flexural strength is increased, such that even thin leads can be cast and extruded without removal of the leads from the casting mold or insertion of the leads into a rotary mechanism leading to breakage or damage of the leads. However, at the same time the good and desired properties, in particular the good application properties, of such leads should not be changed detrimentally.

SUMMARY OF THE INVENTION

The foregoing object is achieved by providing, a method of increasing the tensile strength, breaking strength and flexural strength of colored leads which is characterized in that 1 to 50% by weight of alkyl- and/or hydroxyalkylcellulose whose alkyl radicals may be straight-chain or branched and preferably have 2 to 10 carbon atoms, which is soluble in organic solvents are added to the lead mass.

DETAILED DESCRIPTION

Surprisingly, it has been found that the addition of an alkyl- and/or hydroxyalkylcellulose, also referred to below as cellulose derivative, which is soluble in organic solvents gives the lead mass greater elasticity without impairing the favorable properties of the lead and without detrimentally changing the properties of the other ingredients.

Although it was already known to use water-soluble cellulose derivatives as binders, in particular in the writing utensil industry, the addition of such water-soluble cellulose derivatives does not lead to an increase in the tensile strength and flexural strength of leads.

In addition, EP-A 0 861 657 describes cosmetic masses whose film-forming properties and adhesion properties are said to be improved by the addition of ethylcellulose. In particular, gel-like masses are to be prepared. However, this publication does not achieve the object on which the invention is based.

The basic mass for colored leads usually consists of fatty, wax and oil crude substances. Additives may be added to this basic mass to achieve desired properties. The most important additives are coloring agents, which are added in the form of pigments, color lakes or dyes. In addition, binders and fillers are used to influence the consistency. Where appropriate, preservatives and antioxidants are added to improve the durability and storability. A customary formulation for colored leads comprises, for example, waxes, such as paraffin, beeswax etc., oil raw materials, such as hydrogenated vegetable oil, pigments for coloring, and a solvent which is volatile at body temperature, such as cyclomethicones, which improve the ability of the lead to be applied and, following application, evaporates to leave a durable colored line. The basic mass for the colored lead can, as desired and required, comprise further additives which are known to the person skilled in the art in this field and which require no further explanation here. If paraffin is used for the basic mass, its proportion should not be too high since excessive amounts of paraffin may lead to incompatibilities with the cellulose derivative used according to the invention.

According to the invention, a cellulose derivative, as defined below, is added to a customary basic mass of this type for a colored pencil in order to increase the tensile strength and flexural strength. The proportion of the cellulose derivative can vary depending on the type of basic mass and the processing method. As a rule, a proportion in a range from 1 to 50 parts by weight, based on 100 parts by weight of the basic mass, has proven favorable. An amount of less than 1 part by weight has no significant effect on the strength, while if the proportion is more than 50 parts by weight, the viscosity of the mass may be in a range which is unfavorable for processing.

If the mass is to be extruded under high pressure, the proportion of cellulose derivative may be in the upper range, whereas if the mass is to be shaped by casting, a proportion in the lower range is more favorable. Preferably, not more than 30 parts by weight and particularly preferably not more than 20 parts by weight of the cellulose derivative are added. Particularly favorable results have been achieved with an addition of from 3 to 10 parts by weight of cellulose derivative per 100 parts by weight of lead basic mass.

A cellulose derivative used according to the invention is an alkyl- and/or hydroxyalkylcellulose soluble in organic solvents. To dissolve the cellulose derivatives, organic solvents which can be used are, inter alia, fatty alcohols, fatty acids and esters thereof. Alkyl- and/or hydroxyalkylcelluloses which are soluble in organic solvents are regarded, in particular, as those of which one part dissolves in up to 100 parts of organic solvent at a temperature of 100° C.

Particular preference is given to using cellulose derivatives which are soluble in fatty alcohols or fatty acid esters, in particular those of which 1 g is dissolved in 1 to 100 g of the fatty alcohol, or ester at 100° C.

The alkyl radical of the alkyl- and/or hydroxyalkylcelluloses may be straight-chain or branched and has, for example, 1 to 10 carbon atoms. Preference is given to using cellulose derivatives whose alkyl proportion has 2 to 6, in particular 2 or 3, carbon atoms, since these are readily available. Particular preference is given to using ethylcellulose, optionally mixed with other cellulose derivatives.

The solubility of the cellulose derivatives depends, inter alia, on their degree of substitution. Preference is therefore given to those cellulose derivatives whose degree of substitution is higher than 1.4. Particular preference is given to using ethylcellulose with a degree of substitution of from 2.1 to 2.6 or a mixture of different derivatives with a degree of substitution in this range.

Using the method according to the invention, it is possible to provide a colored lead whose tensile strength and flexural strength have been improved and which also has improved elasticity. It is stable enough to be rotated out in a rotary mechanism without breakage and remains self-supporting. The application properties are good, it being possible, for example, to apply it to skin in a pleasant manner.

Because of this improvement in the mechanical properties, leads can be prepared in which the length to diameter ratio may be greater than 5:1 or 8:1 and even 10:1 and above.

The colored lead is prepared in a manner known per se by mixing and homogenizing the components of the basic mass and the cellulose derivative used according to the invention and then shaping the resulting mass, usually by casting or extrusion, to give a lead. Usually, to prepare the leads, the mass is either poured into molds and, after cooling, removed from the molds, or is introduced into the holding parts of a rotary mechanism, or poured directly into a suitable mold through a holding part and, after cooling, rotated back into the rotary mechanism, or else poured into a suitable section of a rotary mechanism and left to solidify there. Preferably, the colored lead according to the invention is prepared by a casting process.

However, it has been found that cellulose derivatives soluble in organic solvents cannot always be mixed with the basic mass for a colored lead without problems.

Preference is therefore given to using a method for the preparation of colored leads in which an alkylcellulose and/or hydroxyalkylcellulose, soluble in organic solvents, is dissolved in a cosmetically acceptable solvent, the solution is mixed with the pencil mass and further processed in a manner known per se to give a lead.

The cellulose derivative used according to the invention is preferably dissolved in a solvent customary for the field of cosmetics. Preference is given to using a linear or branched fatty alcohol having a chain length of from 7 to 50 carbon atoms, particularly preferably having 12 to 34 carbon atoms and in particular 16 to 24 carbon atoms, a linear or branched, saturated or unsaturated fatty acid, which preferably has a chain length of from 12 to 24 carbon atoms, where the long-chain fatty acids are used particularly at elevated temperature, or an ester of a fatty acid with a shorter-chain alcohol, in particular isopropyl myristate, isopropyl palmitate or myristic acid, optionally in a mixture with fatty alcohols. It is also possible to use mixtures of the above-mentioned alcohols and/or fatty acids and/or esters. Cetyl alcohol, stearyl alcohol, isostearyl alcohol and behenyl alcohol, and mixtures thereof, have proven particularly suitable.

The cellulose derivative is dissolved in the solvent, optionally at elevated temperature, and then the basic mass is added. Since the basic mass is frequently homogenized at elevated temperature, it is preferable to likewise bring the solution comprising the cellulose derivative to this elevated temperature prior to mixing.

The basic mass is mixed with the cellulose derivative and then further processed in a manner known per se, e.g. by extrusion or casting, preferably by casting.

In a preferred embodiment, the cellulose derivative is dissolved in a cosmetically acceptable solvent, preferably a fatty alcohol, a fatty acid ester or an ester of a fatty acid and a fatty alcohol or a mixture thereof, the wax and fatty components are melted, the two are mixed together and homogenized, then, as coloring agents, pigments, color lakes and/or dyes and optionally auxiliaries are added, and the basic mass is then poured into a mold and removed from the mold after cooling.

According to the invention, colored leads are obtained which can be processed without problems due to their improved strength properties compared with leads known hitherto. Since they break neither during preparation nor during use, they can be processed without problems to give pencils.

The invention thus also provides a colored pencil which comprises a lead and a sleeve, where the lead consists of a customary colored lead mass to which 1 to 50% by weight of alkyl- and/or hydroxyalkylcellulose, soluble in organic solvents, have been added. The sleeve consists of natural or synthetic materials.

The colored leads obtained using the method according to the invention are so stable that they can be processed by extrusion and casting and, furthermore, they have a sufficiently high flexural strength and tensile strength for insertion into a rotary mechanism, and can be rotated in and out without breaking. They are likewise suitable to be introduced into sleeve blanks and to be processed to give pencils.

The colored lead obtained according to the invention is preferably used for colored pencils and cosmetics pencils, particularly preferably for cosmetics pencils. Because of its advantageous properties, the colored lead obtained according to the invention may be used for the preparation of eyeliner pencils, kohl pencils, eyebrow pencils and lipliner pencils.

Because of their increased tensile strength and flexural strength, the leads obtained according to the invention are particularly highly suitable for use in cosmetic "liners" which have a rotary mechanism. In such pencils, the leads have a diameter of at most 6 mm, with a length of up to 80 mm. For this reason, the mechanical strength of such pencils is subject to very high requirements; these are, however, met by the colored leads obtained according to the invention.

The invention is illustrated using the examples below.

Example 1

Preparation of an eyeliner pencil

A colored pencil according to the invention was prepared using the formulation given in Table 1. For comparison, a lead was prepared from the identical basic mass, but which lacked the cellulose derivatives essential according to the invention. The formulation for the two masses is given in Table 1 below, all amounts being given in % by weight:

TABLE 1

| INCI Name | Example 1 | Comparative Example 1 |
| --- | --- | --- |
| Colorants | 33.300 | 33.300 |
| Ethylcellulose | 1.500 | — |
| Isostearyl alcohol | 5.900 | 5.900 |
| Stearyl alcohol | 5.900 | 5.900 |
| Hydrogenated vegetable oil | 6.700 | 6.700 |
| Paraffin | 6.700 | 6.700 |
| Cyclomethicone | 40.000 | 41.500 |
| Total | 100.000 | 100.000 |

For the lead of Example 1, the ethylcellulose was added to the mixture of Isostearyl Alcohol and Stearyl Alcohol. The mixture was then heated to 65 to 90° C. with stirring and maintained at this temperature until everything had dissolved. Separately, Hydrogenated Vegetable Oil and Paraffin were melted and then added to the ethylcellulose solution. The pigments were then added and then the total mixture was homogenized in a customary manner. Following the addition of Cyclomethicone, the mass was poured into a mold in a known manner and, following cooling and solidification, removed from the mold. This gave an eyeliner pencil with good delivery, for soft application and good stability.

For comparison, the constituents of the formulation of Comparative Example 1 were mixed in an equivalent manner by melting Hydrogenated Vegetable oil and Paraffin and then adding the pigments and Isostearyl Alcohol and Stearyl Alcohol. Finally, the Cyclomethicone was added to the mass, and the mass was poured into a mold. A mass with comparable delivery was obtained, but it did not have adequate breaking strength. This mass could therefore only be removed from the molds and rotated back into the rotary mechanism with difficulty and with considerable wastage. During application, the leads with a diameter of 2.5 mm broke very readily.

Example 2

Preparation of a lipliner pencil

A mass was prepared for a colored pencil which was suitable for a lipliner pencil. For comparison, a lead for a lipliner pencil was prepared whose basic mass was identical to that of Example 2, but which lack ed the ethylcellulose essential according to the invention. The formulations for both mixtures are given in Table 2 below in each case in % by weight.

TABLE 2

| INCI Name | Example 2 | Comparative Example 2 |
| --- | --- | --- |
| Colorants | 21.300 | 21.300 |
| Ethylcellulose | 3.150 | — |
| Isostearyl alcohol | 5.250 | 5.250 |
| Cetyl palmitate | 5.250 | 5.250 |

TABLE 2-continued

| INCI Name | Example 2 | Comparative Example 2 |
| --- | --- | --- |
| Beeswax | 23.600 | 23.600 |
| Synthetic wax | 3.150 | 3.150 |
| PPG-12/SMDI Copolymer | 1.600 | 1.600 |
| Cyclomethicone | 36.700 | 39.850 |
| Total | 100.000 | 100.000 |

For the lead of Example 2, the ethylcellulose was added to a heated mixture of Isostearyl Alcohol and Cetyl Palmitate, and then the mixture was heated to 65 to 90° C. with stirring and maintained at this temperature until everything had dissolved. Separately, beeswax, synthetic wax and PPG-12/SMDI Copolymer were melted and then added to the ethylcellulose solution. The pigments were then added and then the total mixture was homogenized in a customary manner. Following the addition of cyclomethicone, the mass was poured into a mold in a known manner and, following cooling and solidification, removed from the mold. This gave a lipliner pencil with good delivery, soft application and good stability.

For comparison, the mass according to the formulation of Comparative Example 2 was processed in an equivalent manner. For this, Beeswax, Synthetic Wax and PPG-12/SMDI Copolymer were melted and then pigments, Isostearyl Alcohol, Cetyl Palmitate were added and finally Cyclomethicone was added. The mass was then likewise poured into a mold in a manner known per se and, following cooling and solidification, removed from the mold. The lead obtained using the mass of Comparative Example 2 had a comparable delivery, but had insufficient compressive strength. It could only be removed from the molds and rotated back into the rotary mechanism with difficulty and with considerable wastage.

The examples show that as a result of the addition according to the invention of a cellulose derivative to a customary basic mass for colored pencils, the mechanical properties, in particular the tensile strength and flexural strength, and also the breaking strength, are greatly improved without adversely affecting the advantageous application properties. The leads of the present invention are therefore particularly suitable for pencils with a rotary mechanism, where the lead is subjected to higher mechanical stress than in the case of sharpenable, wood- and plastic-encased pencils. The colored leads according to the invention are of course also suitable for wood- or plastic-encased pencils.

Example 3

Lead masses were prepared from Japan wax, Isostearyl Alcohol and Ethylcellulose, without pigments, in order to test the mechanical properties of leads prepared therefrom. The weak point in the case of thinly cast leads which are inserted into a rotary mechanism is the transition point directly above the lead holder where the leads break preferentially. Masses were prepared with the compositions given below. Using this mass, leads with a diameter of 3 mm and a length of 34 mm were cast and then subjected to various tests.

TABLE

|  | 1 | 2 | 3 |
|---|---|---|---|
| Japan wax (parts by weight) | 50.000 | 50.000 | 50.000 |
| Isostearyl Alcohol (parts by weight) | 25.000 | 25.000 | 25.000 |
| Ethylcellulose (parts by weight) | — | 2.500 | 5.000 |

3.a) Mold test

The resulting mass was poured into sleeve blanks then it was attempted to remove the molding from the mold. Only the leads with formulation 3 could be removed without problems and without auxiliary means, such as release agents, compressed air etc. In the case of the leads with formulation 2, considerable wastage arose. With the mass of formulation 1, no leads could be removed from the molds.

3.b) Casting test

The masses with formulations 1, 2 and 3 were also tested in a rotary mechanism. For this purpose, a partially assembled mechanism was mounted on a metal mold and the mass in each case was then poured into the mold through the holding part. The following result was obtained:

Formulation 1. 20 break off out of 20
Formulation 2. 4 break off out of 20
Formulation 3. 0 break off out of 20

This shows that the lead mass obtained according to the invention has high stability and can be cast and removed from the mold without problems.

3.c) Drop impact test

A drop impact test was carried out with the leads cast from the 3 formulations. For this the complete mechanism with inserted lead was dropped tip-first 3 times from a height of 30 cm in a guide tube onto a hard base. The result of the drop impact test was as follows:

Formulation 1. 20 break off out of 20
Formulation 2. 9 break off out of 20
Formulation 3. 0 break off out of 20

This test shows that the colored lead obtained according to the invention which has excellent strength.

3.d) Tensile test

A tensile test was carried out using leads which had been prepared from the 3 formulations. For this purpose, a tensile force was exerted in the axial direction onto a lead inserted into a rotary mechanism, and the value at which the lead broke off at the holding part was ascertained. The following results were obtained:

Formulation 1. 0.001 N to 0.005 N
Formulation 2. 0.020 N to 0.040 N
Formulation 3. 2.040 N to 3.400 N This test shows that the colored lead obtained according to the invention has excellent tensile strength.

3.e) Flexural test

A flexural test was carried out using the leads obtained from the 3 formulations. For this purpose, the lead was in each case rotated completely out of the rotary mechanism and then, from a distance of 34 mm from the holding part, a force is allowed to act upon the lead. The deflection of the tip of the lead before it breaks off is measured. The following results were obtained:

Formulation 1. not able to be measured
Formulation 2. <1 mm
Formulation 3. 3 mm to 6 mm This test shows that the colored leads obtained according to the invention have excellent flexural strength.

The tests carried out demonstrate that it is possible according to the invention to considerably increase the tensile strength and flexural strength even in the case of very thin leads, meaning that these can be used in rotary mechanisms without problems.

What is claimed is:

1. A method for increasing the strength of a non-water based lead comprising:
    combining a non-water based lead mass and an organic solvent with an additive comprising at least one of an alkyl and a hydroxyalkylcellulose which is soluble in the organic solvent, wherein the additive is present in an amount of between 1 to 50% by weight and the alkyl radicals are one of straight-chain and branch and have from 2 to 10 carbon atoms; and forming a lead from the non-water based lead mass.

2. The method as claimed in claim 1, wherein the additive is present in an amount between 1 to 30% by weight.

3. The method as claimed in claim 2, wherein the additive is present in an amount between 3 to 10% by weight.

4. The method as claimed in claim 2, wherein the additive is ethylcellulose soluble in organic solvents is added.

5. The method as claimed in claim 1, wherein the organic solvent is selected from at least one of a fatty alcohol and a fatty acid ester and wherein the additive is added in an amount of 1:1 and 1:100 with respect to at least one of a fatty alcohol and a fatty acid ester at 100° C.

6. The method as claimed in claim 1, wherein the additive is dissolved in one of a fatty alcohol having a chain length of from 7 to 50 carbon atoms and an ester of a fatty acid having a chain length of from 12 to 24 carbon atoms.

7. The method as claimed in claim 1, wherein in the organic solvent is selected from the group consisting of isopropyl myristate, isopropyl palmitate, myristic acid, cetyl alcohol, stearyl alcohol, isostearyl alcohol, behenyl alcohol and mixtures thereof.

8. The method as claimed in claim 1, including shaping a colored lead having a length to diameter ratio of at least 5:1.

9. The method as claimed in claim 1, including shaping a colored lead having a length to diameter ratio of at least 8:1.

10. The method as claimed in claim 1, including shaping a cosmetic lead from the lead mass.

11. The method as claimed in claim 1, including shaping a lead by casting.

12. A colored pencil comprising a non-water based colored lead and a sleeve, where the lead comprises from 1 to 50% by weight, based on the weight of the lead, of an additive comprising at least one of an alkyl and a hydroxyalkylcellulose having alkyl radicals which are one of straight-chain or branched and have from 1 to 10 carbon atoms, wherein the additive is soluble in an organic solvent.

13. The colored pencil as claimed in claim 12, wherein the colored lead has a diameter of from 1 to 6 mm.

14. The colored pencil as claimed in claim 13, wherein the sleeve is equipped with a rotary mechanism, into which the colored lead is inserted.

15. The colored pencil as claimed in claim 14, wherein the lead is self-supporting.

16. A colored pencil comprising a colored lead having a diameter which is less than or equal to 6 mm and whose length is between 25 to 80 mm, wherein the lead is inserted into a rotary mechanism of a rotating pencil.

17. The colored pencil as claimed in claim 16, wherein the pencil is a cosmetics pencil.

18. The colored pencil as claimed in claim 17, wherein the cosmetics pencil is selected from the group consisting of an eyebrow pencil, kohl pencil, eyeliner pencil and lipliner pencil.

* * * * *